(12) United States Patent
Acker et al.

(10) Patent No.: US 6,508,774 B1
(45) Date of Patent: Jan. 21, 2003

(54) HIFU APPLICATIONS WITH FEEDBACK CONTROL

(75) Inventors: David E. Acker, Setauket, NY (US); Patrick David Lopath, East Setauket, NY (US)

(73) Assignee: Transurgical, Inc., Setauket, NY (US)

( * ) Notice: Subject to any disclaimer, the term of this patent is extended or adjusted under 35 U.S.C. 154(b) by 0 days.

(21) Appl. No.: 09/523,915

(22) Filed: Mar. 9, 2000

Related U.S. Application Data
(60) Provisional application No. 60/123,505, filed on Mar. 9, 1999.

(51) Int. Cl.[7] .................................................. A61N 7/00
(52) U.S. Cl. .............................. 601/2; 601/1; 600/439
(58) Field of Search .......................... 601/1, 2; 600/439

(56) References Cited

U.S. PATENT DOCUMENTS

| | | | |
|---|---|---|---|
| 4,603,702 A | | 8/1986 | Hwang et al. |
| 5,269,306 A | | 12/1993 | Warnking et al. |
| 5,573,497 A | | 11/1996 | Chapelon |
| 5,827,204 A | * | 10/1998 | Grardia et al. ................. 601/2 |
| 6,083,159 A | * | 7/2000 | Driscoll, Jr. et al. ......... 600/371 |
| 6,113,559 A | * | 9/2000 | Klopotek ........................ 601/3 |
| 6,176,840 B1 | * | 1/2001 | Nishimura et al. ............ 601/2 |
| 6,254,553 B1 | * | 7/2001 | Lidgren et al. ................ 601/3 |

FOREIGN PATENT DOCUMENTS
WO     WO00/53263     9/2000

OTHER PUBLICATIONS
K. Hynynen, The Threshold For Thermally Significant Cavitation In Dog's Thigh Muscle in vivo, Ultrasound in Med. and Biol. vol. 17, No. 2, pp. 157–169, 1991.

* cited by examiner

*Primary Examiner*—Marvin M. Lateef
*Assistant Examiner*—Devaang Shah
(74) *Attorney, Agent, or Firm*—Lerner, David, Littenberg, Krumholz & Mentlik, LLP

(57) ABSTRACT

High intensity focused ultrasound heating is provided by applying therapeutic ultrasonic waves using an array of transducers. Cavitation is detected by using some or all of the transducers in the array to detect ultrasonic waves emanating from or reflected from the patient's body or the interface. A feedback signal is generated based on such detection. If the feedback signal indicates the presence of cavitation, the therapeutic ultrasonic waves are terminated or altered. Obstacles to ultrasound transmission, such as bony structures or bubbles at the interface between the transducer array and the patient can be detected using the same transducers.

39 Claims, 2 Drawing Sheets

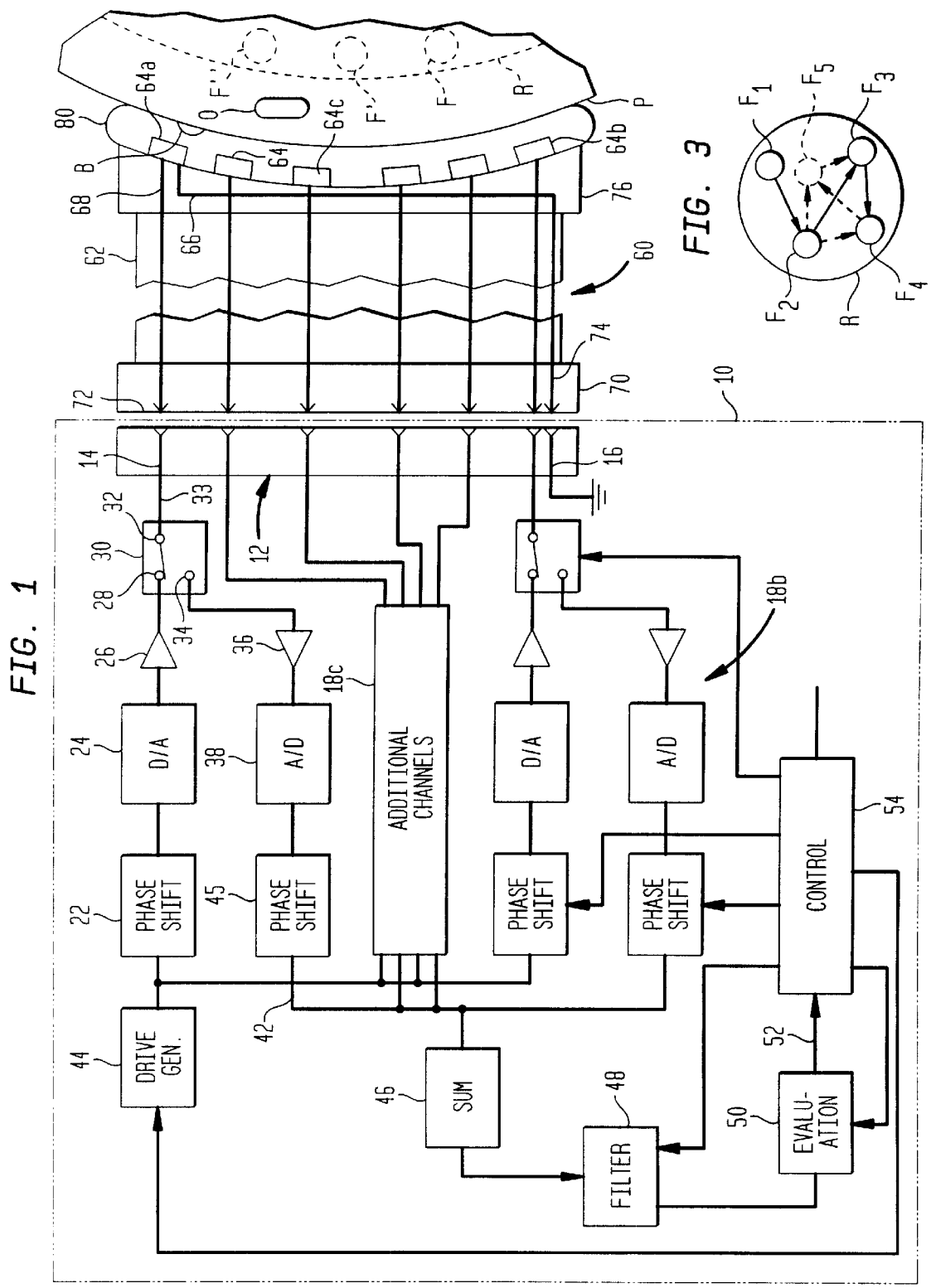

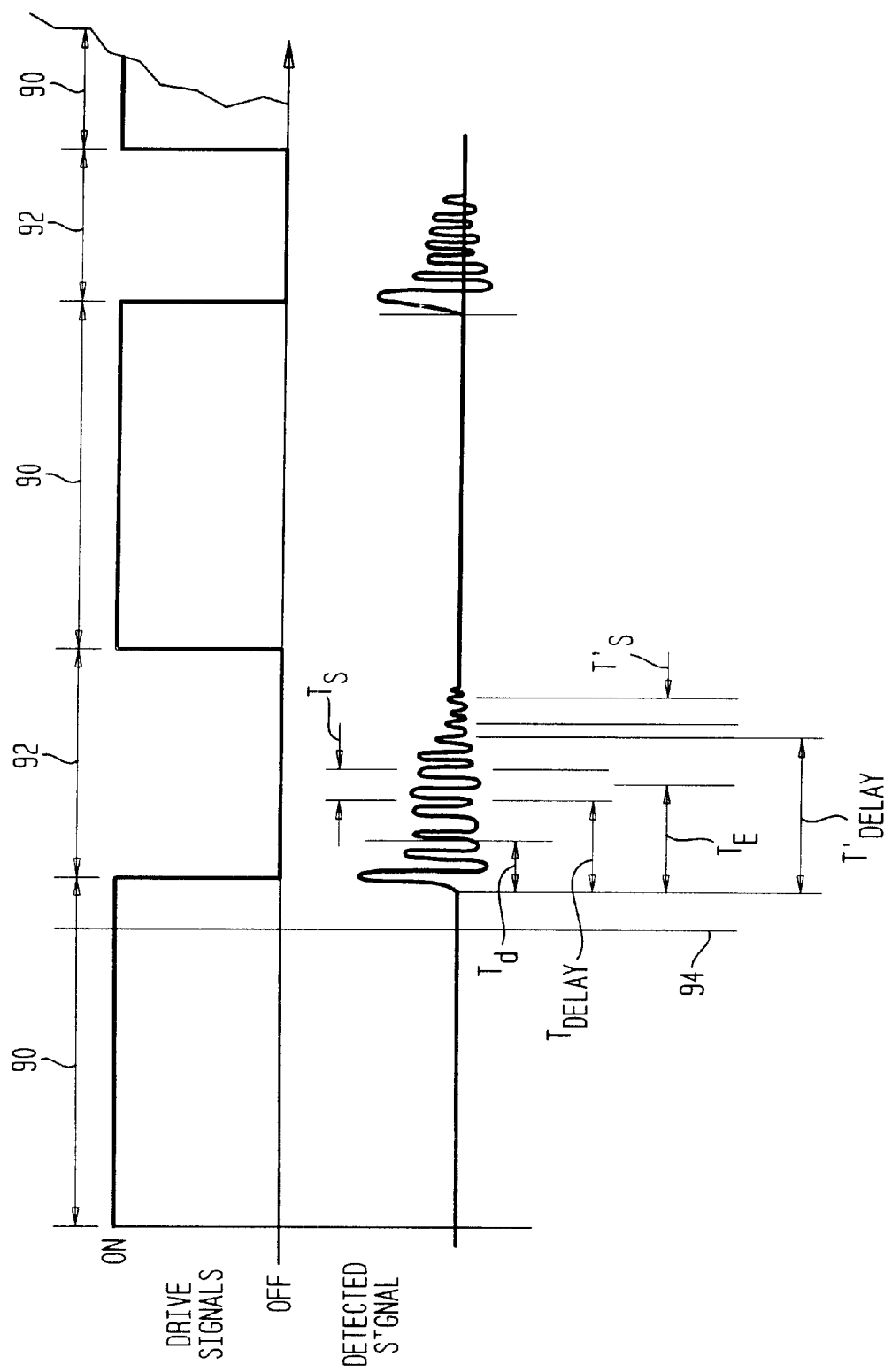

HIFU APPLICATIONS WITH FEEDBACK CONTROL

CROSS-REFERENCE TO RELATED APPLICATIONS

This application claims benefit of U.S. Provisional Patent Application No. 60/123,505, filed Mar. 9, 1999, the disclosure of which is hereby incorporated by reference herein.

FIELD OF THE INVENTION

The present invention relates to apparatus and methods for controlled heating of body tissues by high intensity focused ultrasound, commonly referred to by the acronym HIFU.

BACKGROUND OF THE INVENTION

Elevated temperature treatments are used for a variety of purposes in medical and veterinary practice. In HIFU treatment, ultrasonic energy is focused to a small spot within the body so as to heat the tissues to a temperature sufficient to create a desired therapeutic effect. This technique can be used to selectively destroy unwanted tissue within the body. For example, tumors or other unwanted tissues can be destroyed by applying focused ultrasonic energy so as to heat tissue to a temperature sufficient to kill the tissue, commonly about 60° to about 80° C., without destroying adjacent normal tissues. Other elevated-temperature treatments include selectively heating tissues so as to selectively activate a drug or to promote some other physiological change in a selected portion of the subject's body. The term "heating" is used herein as referring to all of these treatments, whereas the term "ablation" as used herein as specifically referring to procedures in which tissue is deliberately killed.

As disclosed in International Application PCT/US98/1062, published as International Publication WO/98/52465 the disclosure which is hereby incorporated by reference herein, HIFU heating typically is conducted using an ultrasonic emitter having an array of transducers. The transducers are actuated with a drive signal so as to emit therapeutic ultrasonic waves at a selected frequency. Differences in phase can be applied to the drive signal sent to each transducer so that the therapeutic ultrasonic waves tend to reinforce one another constructively at the focal location. As also disclosed in the '465 publication, the transducer array may be incorporated in a disposable device. As described, for example in copending, commonly assigned U.S. patent applications Ser. No. 09/496,988, filed Feb. 2, 2000 and 60/125,676, filed Mar. 22, 1999, the disclosures of which are also incorporated by reference herein, HIFU. may be applied but transducer arrays which are mounted on a probe such as a catheter which can be introduced into the body as, for example, within the vascular system or into a cavernous internal organ.

Application of intense ultrasonic energy to body tissues can result in a phenomenon referred to as "cavitation" in which small bubbles form and collapse. The occurrence of cavitation at any point within the body is dependent upon factors including the local temperature at that point, the composition of the tissue at that point and the characteristics of the ultrasonic energy applied to that point. In some medical procedures, cavitation is regarded as a desirable phenomenon for inducing tissue damage or for breaking up objects such as deposits within the body. However, in typical heating treatments, cavitation is regarded as highly undesirable because it can cause unwanted and unpredictable forms of tissue damage.

Various approaches have been proposed for monitoring cavitation in medical treatments of various types. Cavitation is accompanied by a wide band ultrasonic noise emissions from the region where cavitation is occurring. Vykhodtseva et al., Histologic Effects of High Intensity Focused Ultrasound Exposure with Subharmonic Emission in Rabbit Brain in vivo, Ultrasound in Med. and Biol. Vol. 21, No. 7, pp. 969–979, 1995, employs a hydrophone to monitor ultrasonic noise emission from the brain of rabbit during experimental application of ultrasound. The hydrophone is connected through a filter to an oscilloscope so that the ultrasonic noise emitted at the focal region can be displayed and observed. Grandia et al., U.S. Pat. No. 5,827,204 discloses a system in which cavitation is deliberately produced, and uses a hydrophone for detecting emitted noise with feedback control of the ultrasonic transmitter for the purpose of optimizing cavitation.

Cavitation is also accompanied by an increase in the tendency of the tissue where cavitation occurs to reflect ultrasonic waves as echoes, commonly referred to as "echogenicity". That is, tissues with the bubbles produced in cavitation tend to reflect more ultrasound than the same tissues without such bubbles. Fujimoto et al., U.S. Pat. No. 5,694,936, discloses a system using a separate ultrasonic emitting transducer array for acquiring ultrasonic images of tissues during heating by directing a separate ultrasonic beam through the subject body and monitoring the reflected ultrasound. Areas where cavitation occurs appear as distinct features in such image. The image generated during the therapy is compared to an image taken prior to therapy wherein cavitation is present. If such comparison indicates a difference above a threshold level, the frequency or phase of the therapeutic ultrasonic waves used to produce the heating effect are altered so as to suppress cavitation.

Holland et al., In Vitro Detection of Cavitation Induced by a Diagnostic Ultrasound System, IEEE Transactions on Ultrasonics, Ferroelectrics and Frequency Control, Volume 39, No. 1, pp. 95–101, January, 1992, discloses monitoring of cavitation induced by a diagnostic ultrasound scanner using a separate ultrasonic scanner.

Fry et al., Ultrasound and Microbubbles: Their Generation, Detection and Potential Utilization in Tissue and Organ Therapy—Experimental, Ultrasound in Medicine and Biology, Vol. 21,. No. 9, pp. 1227–1237, 1995, conducts experimental procedures in tissues such as the brain and prostrate of experimental animals. A transrectal probe for producing lesions in the prostate is used to apply ultrasonic energy and also used to acquire ultrasonic images after each individual site exposure. The reference notes that cavitation can be induced "with potential therapeutic possibilities and benefits," but that in certain circumstances the system can be operated in the intensity range which produces thermal lesions without cavitation.

Jing et al, U.S. Pat. No. 5,657,760 teaches the use of an ultrasonic technique for monitoring vaporization of tissue during heating induced by a laser beam so to provide feedback control of the laser beam. The reference suggests broadly that the laser used to provide heating can be replaced by other thermal therapy devices such as electromagnetic devices or ultrasound devices.

Despite all of the effects in the art however, further improvement would be desirable. For example, it would be desirable to provide improved methods and apparatus which can minimize the occurrence of cavitation in HIFU procedures, particularly in HIFU procedures using disposable ultrasonic transducers, and to provide such apparatus and methods in a form suitable for use with small ultrasonic transducer arrays suitable for introduction into small spaces within the body.

SUMMARY OF THE INVENTION

One aspect of the invention provides methods of applying and controlling high intensity focused ultrasound heating within the body of a living subject such as a human or non-human mammal. Methods according to this aspect of the invention desirably include the steps of applying drive signals to a first set of one or more transducers in an array of transducers to thereby cause said first set of transducers to emit therapeutic ultrasonic waves focused at a focal location and thereby heat tissue at such focal location, and acquiring received signals generated by a second set of one or more transducers in said array responsive to ultrasonic waves impinging on said transducers of second set. The received signals can be summed or otherwise processed to provide a detected signal representing ultrasonic waves reflected or emanating from said focal location. Most preferably, one or more of the transducers included in the first or transmitting set for least some part of the drive signal applying step is also included in the second or receiving set during at least some part of the received signal acquiring step. The method according to this aspect of the invention most preferably also includes the steps of producing a feedback signal based on the detected signal indicating whether cavitation has occurred or is likely to occur at within the subject, such as at the focal location, and altering or terminating the emitted therapeutic ultrasonic waves in response to that feedback signal.

The feedback control provided according to this aspect of the invention limits or eliminates the effect of cavitation. This enhanced safety can be used to provide a greater margin of safety for the patient; to allow application of the therapeutic ultrasonic waves at relatively high power closer to the cavitation threshold and thereby provide more effective heating of the tissue, or both. Moreover, because some or all of the same transducers used to emit the therapeutic ultrasonic waves are also used to detect cavitation, there is no need for additional ultrasonic detectors or other elements mounted at the transducer array. This simplifies construction of the transducer array and makes the transducer array more compact. These advantages are particularly useful where the transducer array is disposable or where the transducer array is inserted into the body of the subject.

The selection of transducers included in the first and second sets can be varied during operation so that different transducers are included in the first and second sets at different times during operation. The detected signal can be provided in response to components of the received signals in a detection band of frequencies outside of the drive frequency band.

The method may further include the step of applying monitoring signals in the detection band to at least some of the transducers to produce emitted monitoring ultrasonic waves so that said detected signal represents an echo of the emitted monitoring ultrasonic waves from the focal location. Alternatively, the drive signals can be applied during drive intervals and suspended during one or more receive intervals interspersed with the drive intervals so that application of the therapeutic ultrasonic waves ceases when a sensing interval begins, and the receive signals can be acquired during the receive intervals. A detected signal acquired during each receive interval may represent an echo of the therapeutic ultrasonic waves applied during the immediately preceding drive intervals reflected from said focal location. In a further alternative, the detected signal may represents noise produced by the patient's body. The echoes or noise will increase substantially in amplitude when cavitation occurs. Therefore, the detected signal representing such echoes or noise can be compared to a threshold and the feedback signal indicating cavitation can be issued whenever the amplitude of the detected signal exceeds the threshold.

A method of applying and controlling high intensity focused ultrasound heating according to a further aspect of the invention includes the steps of emitting therapeutic ultrasonic waves so that said emitted waves are focused at a focal location within the body of a subject; providing a detected signal representing ultrasonic waves reflected or emanating from the focal location; and producing a feedback signal based on the detected signal indicating whether cavitation has occurred or is likely to occur at said focal location, and moving the focal location relative to the body of the subject in response to the feedback signal. In preferred methods according to this aspect of the invention, the therapeutic ultrasonic waves are altered by redirecting them to a different focal location when the feedback signal indicates cavitation, rather than reduced in power or terminated. For example, heating of a lesion larger than the focal spot size of the system typically requires movement of the focal location so that various locations within the lesion are heated in sequence. In preferred methods according to this aspect of the invention, one location is heated for a selected time, but if cavitation occurs prior to that time, another location is heated for a time sufficient to allow cavitation to subside at the first location. At or after that time, the therapeutic ultrasound waves can be redirected to the first location. The treatment is not interrupted, and the time required to treat the entire lesion is not appreciably increased by the steps required to suppress cavitation.

Methods of applying and controlling ultrasound to a subject according to a further aspect of the invention desirably include the step of positioning an array of transducers adjacent the body of a subject, as, for example, within the body or on the skin, and coupling the transducers to the body of the subject at an interface. For example, where the transducers are disposed outside of the body, the transducers can be coupled to the body using a conventional fluid-filled bag and sound-transmissive gel to provide a low-reflectivity interface. The method according to this aspect of the invention desirably further includes the steps of actuating one or more of the transducers to emit monitoring ultrasonic waves, detecting echoes of said monitoring ultrasonic waves and generating a feedback signal if said detected echoes include echoes having more than a preselected magnitude and a return time less than a preselected minimum return time less than the return time for echoes reflected from a desired focal location within the subject's body. In this case, the detected echoes indicate sound-reflective obstacles adjacent said one or more of said transducers. The method desirably also includes the step of operating at least some of said transducers to emit therapeutic ultrasonic waves focused at said desired focal location to thereby heat tissue of the subject at such focal location, at a time after application of the monitoring ultrasonic waves and acquisition of the receive signals.

Methods according to this aspect of the invention most preferably further include the step of automatically disabling one or more of the transducers in response to the feedback signal, or generating a human-perceptible alarm signal in response to the feedback signal, or both. The entire treatment can be terminated in response to the feedback signal before the high-powered therapeutic ultrasonic waves are applied or modified to exclude use of a particular transducer which causes a strong echo. Thus, the adverse effects caused by bubbles or other obstacles can be avoided.

Further aspects of the invention provide apparatus capable of carrying out these methods and related methods. Apparatus according to one aspect of the invention includes an ultrasonic emitter including an array of ultrasonic transducers and also includes a drive circuit and sensing circuit connected to said transducers for applying drive signals, monitoring signals or both to transducers in the array as discussed above, for acquiring receive signals from transducers in the array and for providing a detected signal in response to the receive signals representing ultrasonic waves reflected or emanating from the patient's body. Desirably, the drive and sensing circuit operates the transducers so that least some of the same transducers serve as elements of a first set of transducers used to apply the therapeutic ultrasonic waves and also serve, at the same time or at a different time, in a second set of transducers used to acquire the receive signal.

The apparatus desirably includes a feedback control circuit responsive to the detected signal for producing a feedback signal indicating whether cavitation has occurred or is likely to occur at said focal location and adjusting the drive and sensing circuit so as to alter or terminate the therapeutic ultrasonic waves in response to the feedback signal.

The transducer array may be part of a disposable ultrasonic emitter for intrabody or extracorporeal use. Preferably, the drive and sensing circuit and the feedback control circuits are provided as elements of a reusable actuating unit having a connector adapted to connect the actuating unit to the disposable emitter. A further aspect of the invention provides the actuating unit as a separate entity.

BRIEF DESCRIPTION OF THE DRAWINGS

FIG. 1 is a functional block diagram of apparatus in accordance with one embodiment of the invention.

FIG. 2 is a timing diagram of certain signals used in a method according to one embodiment of the invention.

FIG. 3 is a diagrammatic view of focus locations used in a method according to a further embodiment of the invention.

DETAILED DESCRIPTION OF THE PREFERRED EMBODIMENTS

Apparatus in accordance with one embodiment of the invention is schematically depicted in FIG. 1. This apparatus includes a reusable actuating unit 10 having a multi-port conductor 12 defining a plurality of channel terminals 14 as well as a ground connection 16. Each channel terminal 14 is connected to an individual transducer drive channel 18. The individual functional elements of two such channels 18a and 18b are depicted in FIG. 1. The remaining or additional channels 18c incorporate elements identical to those used in channels 18a and 18b. A detailed illustration of these additional channels is omitted in FIG. 1 for clarity of illustration. As discussed further below, each channel is used in conjunction with an individual transducer of an ultrasonic transducer array. Therefore, the number of channels 18 in reusable unit 10 and the number of channel connectors in multi-port connector 12 should be equal to the maximum number of transducers in any ultrasonic array to be used with the system.

Channel 18a has a drive signal input 20 that the receive a drive signal in a digital form, i.e., as a series of values defining the waveform. The drive signal input is connected to a drive phase shifting unit 22 which in turn is connected to a digital to analog converter 24. The output of digital to analog converter 24 is connected to the input of an amplifier 26. The output of amplifier 26 in turn is connected to a first or drive node 28 of a switch 30. Switch 30 has a common node 32 and a receive node 34. The common node 32 is connected to the channel terminal 14 associated with channel 18a. Switch 30 is arranged to connect common node 32 and hence channel terminal 14 either to drive node 28 or to receive node 34. The common node 32 of each switch constitutes the signal input/output node of the channel. Switch 30 desirably is a solid state switch incorporating solid state switching components such as transistors which are electronically controllable and which have a rapid response time.

The receive node 34 of switch 30 is connected to the input of an amplifier 36. The output of amplifier 36 in turn is connected to the input of an analog to digital converter 38. The output of the analog to digital converter 38 is connected to the input of a receive phase shift unit 40. The output of phase shift unit 40 is connected to the receive signal output 42 of the channel.

The drive signal inputs 22 of channels 18 are connected to a drive signal generator 44. The drive signal generator is arranged to produce one or more series of digital values representing a waveform. The receive signal outputs 42 of the individual channels are connected to a summing unit 46 adapted to produce a composite signal representing the sum of the individual signals supplied to the unit. The output of summing unit 46 is connected to a frequency selective digital filter and sampling unit 48.

The output of filter and sampling unit 48 in turn is connected to the input of a threshold evaluation unit 50 adapted to produce a feedback signal on an output 52 when the magnitude of the signal received from filter 48 exceed a selected threshold as discussed below. A control computer 54 is linked to the drive signal generator 44; unit 48; evaluation unit 50; to the phase shift units 22 and 40 of each channel 18 and to the switches 30 of the channels so that the control computer 54 can actuate and control each of these components to perform the functions discussed below.

FIG. 1 illustrates the foregoing components in a functional block diagram form for ease of understanding. However, it should be appreciated that separate hardware components are not necessarily present to perform the various functions. Merely by way of example, the drive generator and drive phase shift units 22 can be integrated in a special purpose or general purpose digital processor which generates individual wave forms for the individual channels for the appropriate phase relationship. Likewise, the summing unit 46 and receive phase shift units 40 of the various channels as well as filter 48 and evaluation unit 50 can be integrated in a special purpose or general purpose digital processor which performs equivalent functions. Some or all of these components can be integrated with the control computer 54.

The system further includes a disposable probe or emitter 60 having a probe body 62 and an array of transducers 64 mounted thereto. Each transducer 64 has a signal input and a ground connection. Each transducer 64 includes a piezoelectric element such as one or more layers of polymeric piezoelectric film having ground and signal electrodes overlying opposite surfaces of the film. Preferably, each transducer includes a plurality of layers of film superposed on one another, each layer of film being disposed between a ground electrode and a signal electrode. Although transducers 64 are illustrated as separate bodies in FIG. 1, these transducers may be constituted by pieces of one or more continuous piezoelectric films. Thus, as described in greater detail in the aforementioned copending applications, a film may be provided with individual electrode pairs covering separate regions of the film. Each such region acts as an individual piezoelectric element. The ground electrode or electrodes of each transducer are connected to a ground connection 66, whereas the signal electrode or electrodes of each transducer are connected to a signal input 68.

Disposable unit 60 also has connector 70 that is adapted to mate with a connector 12 of reusable actuating unit 10. Thus, connector 70 has a number of channel terminals 72 equal to the number of transducers 64 and has a ground terminal 74. The signal input 68 of each transducer 64 is connected to one channel terminal 72 whereas the ground input 66 of all of the transducers 64 are connected to ground terminal 74.

As indicated schematically in FIG. 1, the disposable unit includes a structural element 76 arranged to hold the transducers in predetermined spatial relationship with one another. For example, the body may hold the transducers 64 along a curved locus. As further disclosed in the aforementioned copending commonly assigned applications, the structural element may be a deformable element so that the spatial relationship of the transducers may be varied in a known or reproducible manner. The particular shape of body 62 and structural element 76 depicted is merely for purposes of illustration. Physical arrangements such as those discussed in the aforementioned copending applications may be employed. For example, a disposable unit 60 arranged for positioning outside of the body of the patient may include appropriate elements for fastening the device a positioning unit as disclosed in the aforementioned WO/98/52465 publication. A disposable unit intended to position the transducer array within the body of the patient may include an elongated body such as a catheter having a distal end adapted for insertion into the body, with the structural element 70 and transducers 64 mounted adjacent to distal end of the body.

In a method according to one embodiment of the invention, the body of probe unit 60 is juxtaposed with a living subject such as a medical or veterinary patient P so that the transducers 64 of the transducer array are coupled to the patient's body for transmission of sound therebetween. Depending upon the configuration of the probe, a sound transmitting medium such as a liquid filled bag 80 may be interposed between the transducers and the patient's body. As described in the aforementioned WO/98/52465 publication, the bag may be provided as part of the disposable unit. The connector 70 of the probe is engaged with the connector 12 of the reusable actuator unit 10, thereby connecting the signal terminals 68 of each transducer 64 through one set of engaged terminals 14 and 72 to the signal input/output node 32 of one channel 18 in the actuator unit, so that each transducer is associated with one channel 18.

The control unit 54 actuates the other components of the reusable unit in alternating drive intervals 90 and receive intervals 92 (FIG. 2). At the inception of each drive interval, the control unit causes the switch 30 of each channel to connect the input/output node 32 of that channel, and hence the transducer 64 associated with that channel to the drive node 28. During the drive interval, the control unit actuates drive generator 44 to generate a drive signal at a selected therapeutic drive signal frequency in a drive signal frequency band, typically between about 1–12 MHz. This drive signal is applied through the drive signal input 20 of each channel 18. The control unit 54 actuates the drive phase shift unit 22 of each channel to apply a delay to the drive signal. The delayed or phase shifted drive signal of each channel is converted to analog form by the D/A converter 24 and amplified by the drive signal amplifier 26 of the channel. The various phase shifted drive signals are applied to the individual transducers 64. These drive signals cause the transducers to emit therapeutic ultrasound waves at the drive signal frequency.

The waves emitted by the various transducers have phase relationships dependent upon the delays introduced by the various phase shift units 22 of the individual channels. The delays are selected according to conventional principles so that the therapeutic ultrasound waves reinforce one another at pre-selected focal location F within the patient's body. Stated another way, the differences between the delays applied by the individual channels compensate for differences in time required for sound to propagate from the individual transducers 64 to the focal location. For example, transducer 64a and 64b are relatively far from focal location F and the phase shift units of channels 18a and 18b apply little or no delay to the drive signals applied to those transducers. Transducer 64c is relatively close to the focal location and hence the channel associated with that transducer applies a longer delay so that the therapeutic ultrasound waves from all of these elements are in phase with one another. In certain applications, the delays should also be selected to compensate for phase aberration. That is, where tissues disposed between the transducer array and the focal location are of non-uniform composition, differences in sound propagation velocity along the paths from different transducers to the focal location can introduce differences in propagation time. Using known techniques, the delays applied to the drive signals can be adjusted to compensate for these differences as well, so as to achieve a sharper focus of the therapeutic ultrasonic waves. Attenuation of the mutually-reinforcing waves by the tissue at the focal location, and conversion of the acoustic energy into heat energy, heats the tissue at the focal location.

When drive interval 90 ends and the succeeding receive interval 92 commences, control unit 54 commands the switch 30 of each channel to disconnect its input/output node 32 from output node 28 and to connect the common node of the channel, and hence the associated transducer 64, to the receive node 34. This connects the transducers to the inputs of receive amplifiers 36. Because the transducers 64 are no longer driven, the vibration of the transducers decays rapidly and the transducers stop emitting the therapeutic ultrasonic waves. Once the vibration of the transducer produced by the applied drive signal has decayed, the transducers will act as receiving transducers. That is, ultrasonic sound impinging on the transducers will cause them to vibrate and to generate a voltage on the signal connection 68 of each transducer representing the ultrasonic waves impinging on that transducer.

The signal developed by each transducer is amplified by the receive amplifier 36 of the associated channel 18, converted to digital form and converted to digital form by the A/D converter 38 of that channel. The control unit 54 commands the receive phase shift unit 40 in each channel to apply a delay thereby providing a phase-shifted received signal on the receive signal output 42 of each channel. The phase shifted received signals are summed by summing the unit 46 to yield an aggregate detected signal. As discussed above in connection with the drive signals, the differences between the delays applied by the individual channels compensate for differences in propagation time between focal region F and the various transducers. Therefore, components of the phase shifted received signals representing sound traveling to the various transducers from focal location F will be in phase with one another and will reinforce one another in the aggregate detected signal produced by summing unit 46. Stated another way, the array of transducers 64 acts as a transmitting phased array during the drive intervals and as a receiving phased array reciprocal to the transmitting phased array during the receive intervals. The delays or phase shifts required to accomplish this reciprocity in the receive mode are substantially equal to the delays or phase shifts required in the drive mode. Where the delays applied to the drive signals are adjusted to compensate for phase aberration, similar adjustments can be used for the received signals.

A finite settling interval or delay time $T_D$ is required to accomplish switching between the drive mode and the receive mode and for the vibration of the transducer induced by direct application of the drive signal to decay. During this decay time, the detected signal produced by summing unit 48 represents spurious noise and echoes reflected from regions of the subject's body between the transducer array and the focal location. However, at the end of this decay time, the detected signal begins to represent ultrasonic waves from focal location F. The control unit actuates filter and sampling unit 48 to sample the detected signal during a sampling time $T_S$. Sampling time $T_S$ is selected so that the detected signal represents ultrasonic waves impinging on the transducers during the receive interval 92 but after decay time $T_D$. The sampling time $T_S$ is selected so that it encompasses a time $T_E$ after termination of the preceding drive interval. 90, where $T_E$ is the echo time for the focal region, i.e., the time required for ultrasonic waves at the drive frequency to propagate from the transducers to the focal location and back again. Thus, the detected signal during the sampling time $T_S$ represents an echo from the focal location of the therapeutic ultrasonic waves emitted at a time 94 (FIG. 2) just prior to the end of the immediately preceding drive interval.

Filter and sampling unit 48 suppresses those components of the sampled detected signal at frequencies other than the drive signal frequency. The amplitude of the filtered detected signal during sampling interval $T_S$ thus represents the ultrasonic reflectance or echogenicity of the tissue at focal location F. Evaluation unit 50 determines if the amplitude of this filtered detected signal is equal to or greater than a threshold set by control unit 54 and provides a feedback signal indicating cavitation on output 52 to control unit 54 if the amplitude exceeds the threshold. The threshold is set by control unit 54 so that the normal echogenicity or reflectance of the tissue will not cause the amplitude to exceed the threshold, but enhanced reflectivity of the same tissue will cause the amplitude to exceed the threshold and will cause the evaluation unit to emit the feedback signal.

If the feedback signal does not occur, the control unit 54 returns the channels to drive mode and commences a new drive interval 90 after termination of the receive interval. However, if the feedback signal does occur, the control unit does not commence a new drive interval, but instead terminates operation in drive mode for a pre-selected rest interval required for the effects of cavitation to dissipate.

The processes used to provide the feedback signal in the foregoing embodiment do not require imaging. Accordingly, the apparatus need not incorporate the hardware and software elements required for ultrasonic imaging. In particular, the transducer array need not incorporate separate transducers adapted for imaging. This facilitates construction of a inexpensive and compact disposable transducer array. This advantage is particularly significant where the transducer array is to be positioned within the patient's body. Moreover, the method does not require separate calibration steps to place the locus of sensitivity of the receiving phased array at the focal location used during transmission of the therapeutic ultrasonic waves.

The control system need not terminate drive mode operation in response to a feedback signal indicating that the threshold has been exceeded and hence indicating that cavitation is occurring. Instead, the control system can alter the settings of the drive signal phase shift units 22 to shift the focal region for the next drive interval to a new location and alter the settings of the receive signal phase shift units 40 in the same manner so that heating and cavitation detection occur at the new focal location F'. The new focal location is within the region R to be heated.

As described in the aforementioned WO/98/52465 publication, it is often desirable to heat a relatively large region of tissue, referred to as a pseudofocal region, by applying ultrasonic energy at numerous points in succession so that the ultrasonic energy is effectively swept along a preselected path through the region. As schematically indicated in FIG. 3, the system may be originally set to apply sonic energy along a path leading to a succession of focal locations $F_1$, $F_2$, $F_3$ and $F_4$. The system may be arranged to respond to the feedback signal indicating cavitation by altering this path. For example, if the phase shift units are set to place the focal location momentarily at location $F_2$, and the feedback signal indicates occurrence of cavitation at this location, the control unit may alter the settings to shift the focal location to location $F_3$, the next planned location along the path, or to any other location along the path. Alternatively, the control unit may divert the focal location to a new location $F_5$ within the pseudofocal region but not part of the original path. The control unit may return the focal location to the location $F_2$ where cavitation occurred after an interval sufficient for the effects of cavitation to subside.

The control unit also may alter the characteristics of the drive signals in other ways. For example, the control unit can reduce the amplitude of the drive signals or superimpose an additional component such as a higher frequency component intended to suppress cavitation.

Some systems incorporate mechanical devices for moving the transducer array relative to the patient so as to the focal region within the patient. The control unit 54 may be linked to such mechanical devices to move the focal location in response to the feedback signal indicating occurrence of cavitation.

In a method according to a further embodiment, the system is operated in the same manner except that the sampling interval $T'_S$ occurs later during each receive interval 92. That is, the detected signal from filter and timing unit 48 represents ultrasonic waves impinging on transducers 64 during a sampling interval $T'_S$. The commencement of this sampling interval is delayed after cessation of drive signal application by a delay time $T'_{delay}$ which is greater than the echo time $T_E$. Therefore, the ultrasonic waves impinging on the transducers during interval $T_S$ are waves emanating from focal region F after the echoes from the applied therapeutic ultrasonic waves have substantially subsided. The sound impinging on the transducer element 64 during an interval $T'_S$ and hence the detected signal from filter 48 represents noise emitted by the subject's body.

Cavitation is accompanied by emission of broadband ultrasonic noise. Accordingly, the noise level and the amplitude of the detected signal will increase substantially upon occurrence of cavitation. Because the noise emissions arising from cavitation are broadband emissions, filter and timing unit 48 may be adjusted to select components in the detected signal from summing unit 46 within a detection band of frequencies different from the drive signal band. For example, the detection band may be selected to encompass a harmonic or subharmonic of the drive frequency.

Evaluation unit 50 applies a threshold to the detected signal representing noise emission in substantially the same way as discussed above with respect to the detected signal representing echogenicity. The threshold can be adjusted by control unit 54 to compensate for normal background noise. For example, noise emission in the absence of cavitation can be measured prior to commencement of treatment at a particular focal location or during a receive interval in an early stage of treatment, by measuring the amplitude of the detected signal during such receive interval. The threshold is set slightly above the background level. The threshold can be changed for each new focal location.

In the methods discussed above, all of the transducers 64 are included in a first set of transducers used to apply the therapeutic ultrasound waves during each drive interval and all of the transducers are included in a second set of transducers used to acquire received signals during each receive interval. In methods according to further embodiments of the invention, the control unit 54 selects less than all of the transducers 64 for use as elements of the second or receiving set during each receive interval. During each receive interval, a control computer 54 places only those channels 18 associated with the selected transducers into receive mode. The remaining channels are placed into an idle or inactive state. The detected signal produced by summing unit 46 thus represents received signals from only those transducers included in the second set. The second set may include only one transducer, in which case it is incapable of functioning as a phased array but functions as an omnidirectional microphone. The received signal and hence the detected signal does not particularly emphasize sound emanating from the focal location. However, the noise produced by cavitation at the focal region will still be represented in the receive and detected signals and therefore there will be a substantial difference between the amplitude of the detected signal in the presence of cavitation and the amplitude of the detected signal in the absence of cavitation. A thresholding scheme similar to those discussed above can be employed by evaluation unit 50.

In a method according to a further embodiment of the invention, less than all of the transducers are used to apply the therapeutic ultrasonic waves during some or all of the drive intervals. For example, only those drive elements having relatively good acoustic paths to a particular focal location may be employed during heating of that particular focal location. There may be obstacles O such as bones disposed between some of the drive elements and a particular focal location. As seen in FIG. 1, obstacle O lies along the direct path between transducer 64a and focal location F, whereas no such obstacle is present along the direct path or straight line between transducer 64c and focal location F. Therefore, when the focus of the array is disposed at location F, transducer 64a is omitted from the first set of transducers whereas transducer 64c is included. This allocation may be varied dynamically as the focal location changes. Thus, when the focal location shifts to location F", the obstacle is disposed on the straight line path between transducer 64c and the focal location, but the obstacle is absent from the straight line between transducer 64a and the focal location. Therefore, the control unit selects transducer 64a for inclusion in the first or transmitting set and omits transducer 64c.

During various intervals of the process, the first and second sets may be mutually exclusive. For example, the second or receive set may include only transducers which are excluded from the first set and vice versa. However, as the allocation of transducers to the sets changes at different times during the process, some or all of the transducers serve as elements of the first set during some times and as elements of the second set during other times.

Allocation of transducers to the sets used with different focal locations can be based on previously acquired data such as previously acquiring image data or other advance knowledge of the patient's anatomy. In a further variant of the invention, such allocation is based upon echo detection. In a simple obstruction detection scheme, each transducer is actuated individually in the transmitting mode with monitoring signals and then in the receive mode. The monitoring signals have lower power than the drive signals used to apply the therapeutic ultrasonic waves. The signal acquired by each transducer in receive mode is examined to detect echoes having a delay time shorter than the echo $T_E$, the echo return time from the desired focal location The short-time echoes indicate the presence of reflective obstructions close to the particular transducer. If the short-time echoes exceed a threshold level, a feedback signal indicating presence of significant obstructions associated with the particular transducer is generated. The control unit may disable that transducer during drive mode operation and hence exclude it from the first or transmitting set if the feedback signal is generated, i.e., if echoes having an amplitude above a preset level are received with a return time below a preset minimum substantially less than $T_E$.

Although the discussion above refers to disabling individual transducers, it is also possible to evaluate and selectively disable groups of more than one transducer. For example, transducers which are not the closest transducers to a particular obstacle may give rise to significant echoes from such obstacle. Disabling particular transducers which are affected by reflective obstacles serves to align the first or transmitting set of transducers with a region or "acoustic window" relatively free of highly-reflective obstacles. In a further variant, where the system includes a positioning device capable of moving the transducer array with respect to the patient, the control unit may react to detected obstacles by physically moving the transducer array with respect to the patient. For example, after obstacle detection with the transducer array in one position, and after a decision has been made as to which transducers should be included in or excluded from the first or transmitting set for the transducer array in that location based on obstacle detection, the control unit can determine whether the array meets predetermined criteria as, for example, a minimum number of transducers. If not, the system moves the transducer array or the patient by a selected amount and repeats the process until the criteria are met, whereupon treatment is conducted.

In a further embodiment of the invention, an echo detection scheme similar to that used to detect obstacles is used to detect bubbles at an interface between the therapeutic apparatus and the patient's body. For example, where the therapeutic apparatus is applied to the surface of the skin or other exposed tissue, a bubble B can be present at the interface between the fluid filled bag 80 and the skin.

Typically, a gel or other sound transmissive fluid is applied to the surface of the bag, to the surface of the skin or both to form a bubble-free interface between the bag and the skin. However, imperfections in this procedure can leave bubble B at the interface. Such bubbles are undesirable because they cause reflection of the therapeutic ultrasound and dissipation of substantial amounts of the ultrasound at the interface. This can lead to burning of the skin. Because such bubbles are disposed at the interface with the skin or other exposed tissue, they are located closer to the transducer array than the desired focal location F within the patient. Therefore, these bubbles will give rise to prominent echoes with a short return time. As discussed above with reference to the internal obstacle O, each transducer can be actuated first in the transmit mode and then in the receive mode to provide a detected signal representing echoes of signals from that transducer. That signal is examined and if an echo having an amplitude greater than a selected threshold and a return time shorter than a selected minimum is found, a feedback signal is generated and that transducer, or the entire array, is disabled by the control unit. Alternatively or additionally, the control unit or the evaluation unit can trigger a human-perceptible alarm to signal the operator to stop the procedure. In variants of these approaches, a plurality of transducers can be used as a sparse imagining array to derive an image of the interface and tissues adjacent the transducer array.

In methods according to further embodiments of the invention, the control unit actuates the drive signal generator 44 to generate therapeutic drive signals at a first frequency, in the drive frequency band and to generate monitoring signals in a detection frequency band outside of the drive frequency band. The detection band desirably encompasses higher frequencies than the drive frequency band. The channels 18 associated with a first or transmitting set of transducers of the drive mode continually and the drive signals are applied continually to these channels so that the first set of transducers operate continually in the transmit mode.

The monitoring signal is supplied to channels 18 associated with transducers of a second set. These channels are operated alternately in the transmit and receive mode. When the channels are in the transmit mode, the associated transducers emit monitoring ultrasonic waves at the monitoring frequency. Typically these waves are substantially lower in power than the therapeutic ultrasonic waves. In the receive mode, these transducers receive ultrasonic waves including echoes of the therapeutic waves and echoes of the monitoring waves and accordingly the receive signals from these transducers will include components in the drive frequency band and in the detection band. The receive signals are amplified, digitized, phase shifted and summed as discussed above to provide a detected signal, which is sampled to capture that portion of the detected signal representing an echo of the monitoring waves. Filter and sampling unit 48 is set to set to selectively pass only signal components in the detection band and to suppress signal components in the drive band. The amplitude of the detected signal is compared to a threshold in a manner similar to that discussed above and the feedback indicating the presence of cavitation is issued by evaluation unit 50 if this amplitude exceeds the threshold.

In a further variant of this approach, each terminal 14 of connector 12 and hence each transducer 64 is connected to a complete channel having both receiving and transmitting capabilities and capable of switching between transmit and receive modes, and also connected to the output of a partial channel capable of transmit mode operation only. The transmit mode only channel is used to apply drive signals in the drive frequency band continually, whereas the complete channel is used to apply monitoring signals in the detection frequency band and to receive signals in the detection band. That is, each transducer continually acts as a transmitter in the drive frequency band and acts alternately as a transmitter and a receiver in the detection band. The complete channel may be provided with a frequency selective filter at the input of the receive amplifier 36 so as to isolate the receive amplifier from the powerful drive signals.

Numerous variations of the features described above can be employed. For example, the feedback signal can be derived using means other than the transducers used to apply the therapeutic ultrasonic waves. Thus, a hydrophone, a separate echo detection device or a separate imaging device can be employed. This approach is distinctly less preferred, particularly where the transducer array is disposable or is introduced into the body because it adversely effects the cost, size and complexity of the transducer array.

As these and other variations and combinations of the features discussed above can be utilized without departing from the present invention, the foregoing description of the preferred embodiments should be taken by way of illustration rather than by way of limitation of the invention as defined by the claims.

What is claimed is:

1. Ultrasonic therapy apparatus comprising:

(a) an ultrasonic emitter including an array of ultrasonic transducers;

(b) a drive and sensing circuit connected to said transducers for applying drive signals to a first set of one or more transducers in said array to thereby cause said first set of transducers to emit therapeutic ultrasonic waves so that said emitted waves are focused at a focal location and heat tissue at such focal location and for acquiring received signals generated by a second set of one or more transducers in said array responsive to ultrasonic waves impinging on said transducers of second set to thereby provide a detected signal representing ultrasonic waves reflected or emanating from said focal location, at least some of the same ones of said transducers being included in said first and second sets during operation of said drive and sensing circuits; and (c) a feedback control circuit responsive to said detected signal for producing a feedback signal indicating whether cavitation has occurred or is likely to occur at said focal location and adjusting said drive circuit so as to alter or terminate said emitted therapeutic ultrasonic waves in response to said feedback signal.

2. Apparatus as claimed in claim 1 wherein said drive and sensing circuit is operative to select particular ones of said transducers included in said first and second sets.

3. Apparatus as claimed in claim 2 wherein said drive and sensing circuit is operative to vary said selection of transducers during successive intervals of operation, the transducers constituting said second set during each interval of operation being excluded from said first set during the same interval of operation.

4. Apparatus as claimed in claim 3 wherein said drive and sensing circuit is operative to apply said drive signals in a drive frequency band and to provide said detected signal responsive to components of said receive signals in a detection band of frequencies outside of said drive frequency band, said drive and sensing circuit also being operative to apply monitoring signals in said detection band to at least some of said transducers and thereby produce emitted monitoring ultrasonic waves so that said detected signal represents an echo from said focal location of said emitted monitoring ultrasonic waves.

5. Apparatus as claimed in claim 3 wherein said drive and sensing circuit is operative to apply said drive signals in a drive frequency band and to provide said detected signal responsive to components of said receive signals in a detection band of frequencies outside of said drive frequency band so that said detected signal represents ultrasonic sound in said detection band emanating from said focal location.

6. Apparatus as claimed in claim 3 or claim 4 or claim 5 wherein said drive and sensing circuit is operative to apply said drive signals and to acquire said receive signals simultaneously.

7. Apparatus as claimed in claim 1 wherein said drive and sensing circuit is operative to apply said drive signals during drive irntervals, to suspend application of said drive signals during one or more receive intervals interspersed with said drive intervals, and to acquire said receive signals during said receive intervals.

8. Apparatus as claimed in claim 7 wherein said drive and sensing circuit is operative to include at least one of said transducers both in the first set during one of said drive intervals and in the second set during one of said receive intervals immediately succeeding that one of said drive intervals.

9. Apparatus as claimed in claim 8 wherein said drive and sensing circuit is operative to include all of said transducers in said first set during each one of said drive intervals and to include all of said transducers in the second set during each one of said receive intervals.

10. Apparatus as claimed in claim 7 wherein said drive and sensing circuit is operative to provide said detected signal for each said receive interval so that the detected signal for each said receive interval represents an echo of the therapeutic ultrasonic waves applied during the immediately preceding one of said drive intervals reflected from said focal location.

11. Apparatus as claimed in claim 1 wherein said drive and sensing circuit is operative to apply said drive signals in a drive frequency band and to provide said detected signal responsive to components of said received signals in a detection band of frequencies outside of said drive frequency band.

12. Apparatus as claimed in claim 11 wherein said drive and sensing circuit is operative to apply said drive signals and to acquire said received signals simultaneously.

13. Apparatus as claimed in claim 1 wherein said array of transducers is adapted for insertion into the body of a mammalian subject.

14. Apparatus as claimed in claim 1 wherein said array of transducers is deformable.

15. Apparatus as claimed in claim 1 wherein said transducers are polymeric piezoelectric transducers.

16. Ultrasonic therapy apparatus comprising:
(a) an ultrasonic emitter;
(b) a drive circuit connected to said transducers for applying one or more drive signals to said emitter to thereby cause said emitter to emit therapeutic ultrasonic waves so that said emitted waves are focused at a focal location;
(c) means for moving said focal location relative to a body of a patient;
(d) means for providing a detected signal representing ultrasonic waves reflected or emanating from said focal location; and
(e) a feedback control circuit responsive to said detected signal for producing a feedback signal indicating whether cavitation has occurred or is likely to occur at said focal location and adjusting said moving means so as to move said focal location relative to the body of the patient in response to said feedback signal.

17. Apparatus as claimed in claim 16 wherein said emitter includes a plurality of transducers, said drive circuit is operative to apply a plurality of drive signals to said transducers so that different ones of said drive signals are applied to different ones of said transducers, and said moving means is operative to adjust said drive circuit so as to vary the phases of said drive signals relative to one another.

18. Apparatus as claimed in claim 16 wherein said moving means is operative to sweep said focal location through a pseudofocal region of the patients body according to a preselected pattern and to alter said pattern responsive to said feedback signal.

19. A method of applying and controlling high intensity focused ultrasound heating comprising:
(a) applying drive signals to a first set of one or more transducers in an array of transducers to thereby cause said first set of transducers to emit therapeutic ultrasonic waves focused at a focal location and thereby heat tissue at such focal location;
(b) acquiring receive signals generated by a second set of one or more transducers in said array responsive to ultrasonic waves impinging on said transducers of second set to thereby provide a detected signal representing ultrasonic waves reflected or emanating from said focal location, one or more of said transducers being included in said first set at at least some part of said drive signal applying set and included in said second set during at least some part of said acquiring step; and
(c) producing a feedback signal based on said detected signal indicating whether cavitation has occurred or is likely to occur at said focal location and adjusting said drive circuit so as to alter or terminate said emitted therapeutic ultrasonic waves in response to said feedback signal.

20. A method as claimed in claim 19 further comprising the step of selecting particular ones of said transducers included in said first and second sets and varying such selection of transducers during successive intervals of operation.

21. A method as claimed in claim 19 wherein said drive signals are in a drive frequency band and said detected signal is provided responsive to components of said received signals in a detection band of frequencies outside of said drive frequency band.

22. A method as claimed in claim 21 further comprising the step of applying monitoring signals in said detection band to at least some of said transducers to produce emitted monitoring ultrasonic waves so that said detected signal represents an echo from said focal location of said emitted monitoring ultrasonic waves.

23. A method as claimed in claim 19 wherein said detected signal represents noise produced by the patient's body.

24. A method as claimed in claim 19 wherein said drive signals are applied during drive intervals, application of said drive signals is suspended during one or more receive intervals interspersed with said drive intervals, and said receive signals are acquired during said receive intervals.

25. A method as claimed in claim 24 wherein said detected signal is acquired during each said receive interval and the detected signal acquired during each said receive interval represents an echo of the therapeutic ultrasonic waves applied during the immediately preceding one of said drive intervals reflected from said focal location.

26. A method as claimed in claim 19 wherein said received signals are acquired during application of said drive signals.

27. A method as claimed in claim 26 wherein said drive signals are in a drive frequency band and said detected signal is provided responsive to components of said received signals in a detection band of frequencies outside of said drive frequency band.

28. A method as claimed in claim 19 wherein said array of transducers is disposed within the body of a living subject.

29. A method as claimed in claim 19 wherein said array of transducers is deformable.

30. A method as claimed in claim 19 further comprising the step of discarding and replacing said array of transducers.

31. A method of applying and controlling high intensity focused ultrasound heating comprising:
(a) emitting therapeutic ultrasonic waves so that said emitted waves are focused at a focal location within the body of a mammalian subject;
(b) providing a detected signal representing ultrasonic waves reflected or emanating from said focal location; and
(c) producing a feedback signal based on said detected signal indicating whether cavitation has occurred or is likely to occur at said focal location and moving said focal location relative to the body of the subject in response to said feedback signal.

32. A method as claimed in claim 31 further comprising the step of sweeping said focal location through a pseudo-focal region of the patient's body according to a preselected pattern, said step of moving the focal location including altering said pattern responsive to said feedback signal.

33. A method of applying and controlling ultrasound to a subject comprising the steps of:
(a) positioning an array of transducers adjacent the body of a subject and coupling said transducers to the body of the subject at an interface;
(b) actuating a set of less than all of said transducers to emit monitoring ultrasonic waves;
(c) detecting echoes of said ultrasonic waves and generating a feedback signal if said detected echoes include echoes having more than a preselected magnitude and a return time less than a preselected minimum return time less than the return time for echoes of said monitoring ultrasonic waves reflected from a desired focal location, whereby said feedback signal indicates sound-reflective obstacles adjacent said set of said transducers;
(d) repeating said actuating and detecting steps using different sets of said transducers in said array in different repetitions;
(e) disabling transducers in those sets for which a feedback signal is generated in said detecting step; and
(f) operating at least some of said transducers in said array other than transducers in disabled sets to emit therapeutic ultrasonic waves focused at said desired focal location to thereby heat tissue of the subject at such focal location.

34. A method as claimed in claim 33 wherein said step of detecting echoes is performed using at least some of said transducers.

35. A method of applying and controlling ultrasound to a subject comprising the steps of:
(a) positioning an array of transducers adjacent the body of a subject and coupling said transducers to the body of the subject at an interface;
(b) actuating one or more of said transducers to emit monitoring ultrasonic waves;
(c) detecting echoes of said ultrasonic waves and generating a feedback signal if said detected echoes include echoes having more than a preselected magnitude and a return time less than a preselected minimum return time less than the return time for echoes of said monitoring ultrasonic waves reflected from a desired focal location, whereby said detected echoes indicate sound-reflective obstacles adjacent said one or more of said transducers,
wherein said actuating step includes applying monitoring drive signals to a set of said transducers including less than all of said transducers so that said set of said transducers emits said monitoring ultrasonic waves, said step of detecting echoes including terminating application of said monitoring drive signals and then acquiring received signals from said set of said transducers representing ultrasonic waves impinging on the transducers in said set.

36. A method as claimed in claim 35 wherein said steps of applying drive monitoring drive signals and acquiring received signals are repeated cyclically, using different sets of said transducers in different cycles, until such steps have been performed using sets including allow said transducers.

37. A method as claimed in claim 36 wherein the set of transducers used in each said cycle includes only one of said transducers.

38. A method of applying and controlling ultrasound to a subject comprising the steps of:
(a) positioning an array of transducers adjacent the body of a subject and coupling said transducers to the body of the subject at an interface;
(b) actuating one or more of said transducers to emit monitoring ultrasonic waves
(c) detecting echoes of said ultrasonic waves and generating a feedback signal if said detected echoes include echoes having more than a preselected magnitude and a return time less than a preselected minimum return time less than the return to me for echoes of said monitoring ultrasonic waves reflected from a desired focal location, whereby said detected echoes indicate sound-reflective obstacles adjacent said one or more of said transducers, wherein said obstacles include air bubbles at said interface.

39. A method as claimed in claim 38 further comprising the step of generating a human-perceptible alarm signal in response to said feedback signal.

* * * * *

UNITED STATES PATENT AND TRADEMARK OFFICE
CERTIFICATE OF CORRECTION

PATENT NO. : 6,508,774 B1
DATED : January 21, 2003
INVENTOR(S) : David E. Acker and Patrick David Lopath It is certified that error appears in the above-identified patent and that said Letters Patent is hereby corrected as shown below:

Title page, Item [54] and Column 1, lines 1-2,
Title, "HIFU APPLICATIONS WITH FEEDBACK CONTROL" should read
-- HIFU APPLICATIONS WITH FEEDBACK CONTROL USING BUBBLE DETECTION --.

Column 1,
Line 35, "as used" should read -- is used --.

Column 3,
Line 25, "for least" should read -- for at least --.

Column 4,
Line 4, "may represents" should read -- may represent --.

Column 5,
Line 20, "least some" should read -- at least some --.

Column 6,
Line 1, "that the receive" should read -- receives --.
Line 38, "48 exceed" should read -- 48 exceeds --.

Column 7,
Line 36, "device a" should read -- device to a --.

Column 10,
Line 49, "so as to the" should read -- so as to move the --.

Column 13,
Line 36, "mode continually" should read -- mode operate continually --.
Line 58, "set to set to" should read -- set to --.

Column 16,
Line 16, "patients" should read -- patient's --.

UNITED STATES PATENT AND TRADEMARK OFFICE
CERTIFICATE OF CORRECTION

PATENT NO. : 6,508,774 B1
DATED : January 21, 2003
INVENTOR(S) : David E. Acker and Patrick David Lopath It is certified that error appears in the above-identified patent and that said Letters Patent is hereby corrected as shown below:

<u>Column 18,</u>
Line 36, "including allow" should read -- including all of --.
Line 51, "return to me" should read -- return time --.

Signed and Sealed this

Twentieth Day of April, 2004

JON W. DUDAS
*Acting Director of the United States Patent and Trademark Office*